(12) United States Patent
DeRidder

(10) Patent No.: US 8,731,678 B2
(45) Date of Patent: *May 20, 2014

(54) PERIPHERAL NERVE STIMULATION TO TREAT AUDITORY DYSFUNCTION

(71) Applicant: Advanced Neuromodulation Systems, Inc., Plano, TX (US)

(72) Inventor: Dirk DeRidder, Dunedin (NZ)

(73) Assignee: Advanced Neuromodulation-Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,030

(22) Filed: Apr. 29, 2013

(65) Prior Publication Data

US 2013/0238070 A1  Sep. 12, 2013

Related U.S. Application Data

(63) Continuation of application No. 12/610,758, filed on Nov. 2, 2009, now Pat. No. 8,433,418, which is a continuation of application No. 11/254,597, filed on Oct. 20, 2005, now Pat. No. 7,613,519.

(60) Provisional application No. 60/620,827, filed on Oct. 21, 2004, provisional application No. 60/631,091, filed on Nov. 24, 2004.

(51) Int. Cl.
*A61N 1/36* (2006.01)

(52) U.S. Cl.
USPC .......................................................... 607/55

(58) Field of Classification Search
USPC ...................... 607/1–2, 45, 55–57, 116, 139
See application file for complete search history.

(56) References Cited

U.S. PATENT DOCUMENTS 8,433,418 B2 *  4/2013  DeRidder ....................... 607/55

* cited by examiner

*Primary Examiner* — Amanda Patton

(57) ABSTRACT

A system and/or method for treating auditory dysfunction by somatosensory system stimulation. The system and/or method comprises a probe and a device to stimulate the probe. The probe has a stimulation portion implanted in communication with a predetermined peripheral nerve site. The stimulation portion of the probe may be implanted in contact with a peripheral nerve dorsal root ganglia, cranial nerve or dermatome area, for example C2 dermatome area or a trigeminal dermatome area. The stimulation portion may be a laminotomy, paddle, surgical, or multiple electrode lead. The device to stimulate the probe may be implanted subcutaneously or transcutaneously.

10 Claims, 9 Drawing Sheets

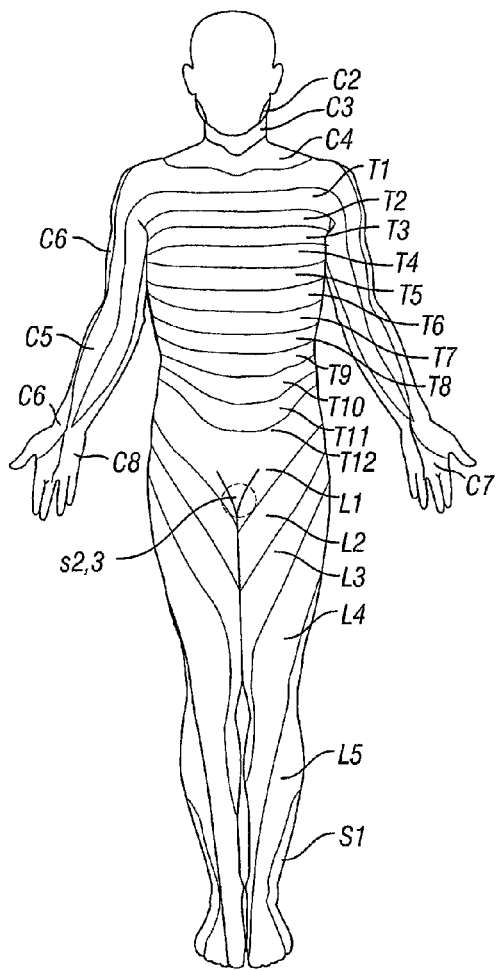 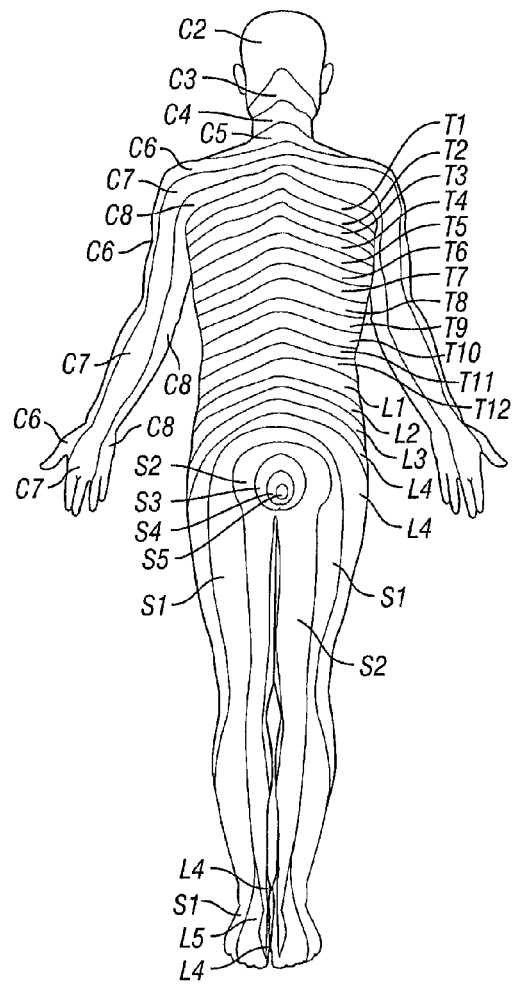
*FIG. 7A*        *FIG. 7B*

PERIPHERAL NERVE STIMULATION TO TREAT AUDITORY DYSFUNCTION

RELATED APPLICATIONS

This application is a continuation of U.S. patent application Ser. No. 12/610,758, filed Nov. 2, 2009 (issued as U.S. Pat. No. 8,433,418) which is a continuation of U.S. patent application Ser. No. 11/254,597, filed Oct. 20, 2005 (issued as U.S Pat. No. 7,613,519), which claims priority to U.S. Provisional Application Nos. 60/620,827 filed Oct. 21, 2004 and 60/631,091 filed Nov. 24, 2004 all of which are incorporated herein by reference.

This application is also related to U.S. Provisional Application Nos. 60/620,762 filed Oct. 21, 2004, 60/631,085 filed Nov. 24, 2004, 60/620,847 filed Oct. 21, 2004, 60/631,089 filed Nov. 24, 2004, and 60/639,365 filed Dec. 27, 2004 each of which is incorporated by reference in its entirety.

TECHNICAL FIELD

This invention relates to neuronal tissue stimulation for medical treatment, and more particularly to stimulating peripheral nerves to treat auditory dysfunction.

BACKGROUND OF THE INVENTION

Hearing clarity is taken for granted by most people; however, temporary periods of altered auditory perception are a normal part of existence. Nearly every individual will experience phantom noises such as "ringing in the ears" during their lifetime as a result of exposure to external and/or internal stimuli. Loud noise (reported by Zhang et al., Wallhausser-Franke et al.), certain pharmaceuticals, stress, and various physical conditions can all cause altered auditory perception, usually on a temporary basis. However, for some individuals with auditory dysfunction, altered auditory perception can be permanent.

Auditory dysfunctions are common. For example, in the United States, the prevalence of tinnitus when the whole population is considered is approximately 3%. This prevalence is only 1% under the age of 45 but increases significantly with age, rising to 9% in the population over 65 years (Adams et al., 1999). This roughly translates to 36 million Americans with tinnitus (Heller 2003). Tinnitus is a noise in the ears, often described as ringing, buzzing, roaring, or clicking. Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the intensity of the perceived noise.

Because auditory dysfunction often occurs secondary to a pathological state, initial treatment may focus on finding an underlying cause. A subject presenting with, for example, tinnitus may be asked for information regarding medications, recent or chronic noise exposure, and home and work environment. Common medications such as aspirin are known to cause tinnitus in some patients or in elevated dosages. Stress can be a direct cause of tinnitus and can aggravate existing cases. A thorough physical exam is typically made of a subject with complaints of tinnitus to eliminate pathologies such as hypertension, tumors, and infections. Objective tinnitus may be diagnosed using a stethoscope if the source of the noise can be localized. For example, hypertension or arterial disorders may produce objective tinnitus, as the carotid arteries pass close to the auditory organs in humans, and excessive pressure or arterial blockage may cause detectible noise to both the subject and to an outside observer.

If a treatable underlying cause to auditory dysfunction symptoms is identified, treatment may focus on elimination of the cause. For example, hypertensive patients may see a reduction or elimination of tinnitus once anti-hypertensive therapy begins. However, a significant number of patients have untreatable underlying pathologies or have auditory dysfunction in the absence of any identifiable cause. For these patients, treatments for directly reducing or eliminating the auditory dysfunction are desirable.

Tinnitus research is actively pursued in the hope of finding efficacious treatments. Recently published work has utilized drug delivery systems such as the system described in U.S. Pat. No. 5,713,847, which includes a catheter inserted into a patient's auditory cortex or thalamus for microinfusing drugs. Another example of published drug delivery techniques is U.S. Pat. No. 6,656,172, which describes a tinnitus treatment that includes inserting intrathecally a catheter for infusing a drug. Other treatment methods may try to mask the perceived tinnitus noise by generating an audible signal of appropriate frequency. WO 01/08617 describes a system with a vibrating probe placed in proximity to the inner ear.

Nerve stimulation has been shown to be helpful in treating patients with chronic intractable pain. For those patients who prove unresponsive to conservative pain management techniques, peripheral nerve stimulation may be a successful therapy for pain management when the pain is known to result from a specific nerve. Peripheral nerve stimulation is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. Subsequent refinements in the technology, surgical technique and patient selection have led to improved long term results.

The use of certain stimulating electrodes to mask tinnitus has been published. U.S. Pat. Nos. 5,735,885 and 5,496,369 describe the placement of an electrode in the primary auditory cortex of a patient. U.S. Pat. Nos. 6,456,886 and 5,697,975 also use an electrode placed in the auditory cortex, and further describe placement of an electrode in the medial geniculate body of the thalamus.

BRIEF SUMMARY OF THE INVENTION

Peripheral nerves carry both motor and sensory information to and from the brain. The present invention comprises a therapeutic system for treating auditory dysfunction having a surgically implanted device in communication with a predetermined peripheral nerve. The device can include a distal probe, such as, for example, an electrode assembly or electrical stimulation lead. The proximal end of the probe is coupled to an electrical signal source, which, in turn, is operated to stimulate the predetermined peripheral nerve.

The predetermined site can be, for example, but not limited to a dermatome area, for example, C2, C3, C4, C5, C6, C7, C8, as well as any thoracic, lumbar or sacral dermatome. Cervical nerve roots (e.g., C1, C2, C3, C4, C5, C6, C7 and C8) and cranial nerves (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve) to provide therapeutic treatments according to the instant invention. Other dermatomes that can be included in the present invention include dermatomes associated with cranial nerves having somatosensory function, for example, but not limited to dermatomes associated with the trigeminal nerve, intermediate part of the facial nerve, glossopharyngeal nerve, or vagal nerve. Other peripheral nerves are spinal nerves such as the suboccipital nerve, the greater occipital nerve, the lesser occipital nerve, the greater auricular nerve, the lesser auricular nerve, the phrenic nerve, and the brachial plexus, which branches to form the dorsal scapular nerve, the thoracic nerve, the suprascapular nerve, the lateral pectoral, the musculocutaneous nerve, the axillarily nerve, the radial nerve, the median nerve, the ulnar nerve, and other minor peripheral nerves, as well as sympathetic and parasympathetic nerves. Yet further, other peripheral nerves also includes thoracic nerve roots (e.g., T1, T2, T3, T4, T5, T6, T7, T8, T9, T10, T11, T12), lumbar nerve roots (L1, L2, L3, L4, L5) sacral nerve roots (e.g., S1, S2, S3, S4, S5) and the coccygeal nerve.

Embodiments of the invention can operate with various stimulation parameters. One example of stimulation parameters used to treat auditory dysfunctions, such as, for example, tinnitus, may use an amplitude in the range of about 2 mA to about 100 mA, a frequency in the range of about 3 Hz to about 80 Hz, and a pulse width in the range of about 5 microseconds to about 100 microseconds. However, other parameters are used in other embodiments of the invention, such as, for example, higher and lower frequencies, various current amplitudes, and/or pulse width durations. In another embodiment of the invention, a frequency stimulation parameter of about 80 Hz is used. Burst mode stimulation is used in preferred embodiments of the invention. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. More particularly, the maximum inter-spike interval may be about 5 milliseconds. Those of skill in the art realize that this can vary depending upon the patient and the treatment. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, in the range of about 10 milliseconds to about 300 milliseconds, or any range therebetween. Preferably, the minimum inter-burst interval may be about 20 milliseconds. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

Embodiments of the invention also comprise methods for treating auditory dysfunction. The method comprises surgically implanting an electrical stimulation lead such as a laminotomy lead, paddle, surgical, or multiple electrode lead. Following implantation, the proximal end of the lead is attached to a signal generator. The signal generator then generates a signal that stimulates a predetermined peripheral nerve. The stimulation of the peripheral nerve modulates components of the somatosensory system that in turn modulate components of the auditory system's extralemniscal pathway.

In some embodiments of the invention, the stimulation parameters are varied after implantation to optimize treatment of an auditory dysfunction. The parameters varied may include modification of the predetermined implantation site, or modification of, for example, signal amplitude, frequency, pulsewidth or pulse shape of the stimulation signal.

Other stimulation devices used in certain embodiments are drug pumps which provide chemical stimulation of a predetermined peripheral nerve. Chemical stimulation can be provided by delivery of pharmaceuticals or neuroactive substances that, for example, disrupt, block, stimulate, and/or modulate peripheral nerve activity.

Magnetic stimulation of predetermined peripheral nerve sites for the treatment of auditory dysfunction is used in certain embodiments of the present invention. Magnetic stimulation can be provided by internally implanted probes or by externally applied directed magnetic fields.

Yet further, thermal stimulation can be provided via implanted probes that are regulated to heat and/or cold temperatures. In other embodiments, ultrasound stimulation is used as a stimulation source, either by itself or in combination with another stimulation source. For example, in certain embodiments of the invention, ultrasound is used to stimulate active tissue by propagating ultrasound in the presence of a magnetic field as described by Norton (2003), herein incorporated by reference in its entirety. Combinations of stimulation sources are used in some embodiments of the invention.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIGS. 7A-7B illustrate examples of the C2 dermatome area; FIG. 7A and FIG. 7B show the cervical dermatomes, including C2 and C3 dermatome.

DETAILED DESCRIPTION OF THE INVENTION

I. Definitions

Figure 1A:
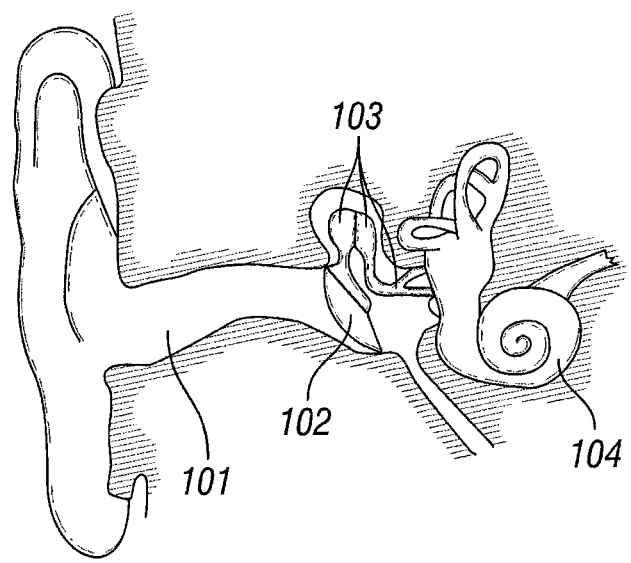
FIGS. 1A-1B are illustrations of the human auditory system including neural connections.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more", "at least one", and "one or more than one." Still further, the terms "having", "including", "containing" and "comprising" are interchangeable and one of skill in the art is cognizant that these terms are open ended terms.

As used herein, the term "auditory dysfunction" refers to conditions or dysfunctions associated with the auditory pathway. Such auditory dysfunctions can include, but are not limited to tinnitus, hyperacousis, phonophobia, misophonia, auditory agnosia in all its forms (verbal and/or non-verbal), auditory spatial dysfunction (localizing sound) and auditory hallucinations, inclusive of musical hallucinosis. Auditory hallucinations can occur in schizophrenia or use of certain drugs (e.g., antimuscarinic agents, antiparkinsonian drugs, antidepressants, beta adrenoceptor antagonists and opiates). Auditory dysfunction can also include hearing loss. Hearing loss can be conductive hearing loss (mechanical transmission of sound into the sensory receptors in the cochlea is impaired), sensorineural hearing loss (a loss of function in the sensory receptors in either the cochlea or the auditory nerve), or central hearing loss (a lesion in the brain stem or auditory cortex).

As used herein, the terms "auditory nerve" and "cochlear nerve" are interchangeable and refer to the nerve fibers along which the sensory cells of the ear communicate information to the brain. The auditory or cochlear nerve are part of the vestibulocochlear nerve which carries two kinds of sensation, vestibular (balance) and audition (hearing) from sensory receptors in the inner ear. The auditory nerve consists of the vestibular nerve and the cochlear nerve. The vestibulocochlear nerve is also known as the eighth cranial nerve.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if a stimulation signal results in a modulation of neuronal activity. For example, the predetermined site is selected in the present invention such that a stimulation lead in communication with a peripheral nerve will stimulate the peripheral nerve when a stimulation signal is applied to the stimulation lead.

As used herein, the term "dermatome" refers to the area of skin innervated by a single dorsal root. One of skill in the art realizes that the boundaries of dermatomes are not distinct and in fact overlap because of overlapping innervations by adjacent dorsal roots. Dermatomes are divided into sacral (S), lumbar (L), thoracic (T) and cervical (C). Yet further, as used herein, the term "dermatome" includes all the neuronal tissues located within the region or adjacent the dermatome area, for example, it may include any peripheral nerve, for example, any cervical nerve root (C1, C2, C3, C4, C5, C6, C7 and C8) that may innervate the dermatome, any and cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve) that may innervate the dermatome. Other dermatomes that can be included in the present invention include dermatomes associated with cranial nerves having somatosensory function, for example, but not limited to dermatomes associated with the trigeminal nerve, intermediate part of the facial nerve, glossopharyngeal nerve, or vagal nerve. Thus, while to some, dermatomes may have a meaning that relates specifically to sensory neurons, as used herein, this limitation should not be applied, but rather the broader description used herein should be used.

As used herein, the use of the words "epidural space" or "spinal epidural space" is known to one with skill in the art, and refers to an area in the interval between the dural sheath and the wall of the spinal canal.

As used herein, the term "C2 dermatome area" refers to the area or the dermatome that covers the occiput or occipital area and the top portion of the neck. Yet further, C2 dermatome area includes the neuronal tissue that is located within this area, for example, the C2 dermatome area and its branches innervate the C2 dermatome, as well as any cervical nerve root and/or cranial nerve that may innervate this area. Thus, the C2 dermatome area may also be referred to as the occiput or occipital area, which refers to the back of the head.

As used herein the term "modulate" refers to the ability to regulate positively or negatively neuronal activity. Thus, the term modulate can be used to refer to an increase, decrease, masking, altering, overriding or restoring of neuronal activity.

As used herein, the term "burst firing" or "burst mode" or "burst mode stimulation" refers to an action potential that is a burst of high frequency spikes (300-1000 Hz) (Beurrier et al., 1999). Burst firing acts in a non-linear fashion with a summation effect of each spike. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter.

Yet further, those of skill in the art also realize that the spike rate within the burst does not necessarily occur at a fixed rate; this rate can be variable.

As used herein, the term "tonic firing" or "tonic mode" refers to an action potential that occurs in a linear fashion.

As used herein, the term "spike" refers to an action potential. Yet further, a "burst spike" refers to a spike that is preceded or followed by another spike within a short time interval (Matveev, 2000), in otherwords, there is an inter-spike interval, in which this interval is generally about 10 ms but can be shorter or longer, for example 5 milliseconds or 0.5 milliseconds.

As used herein, the term "neuronal" refers to a neuron which is a morphologic and functional unit of the brain, spinal cord, and peripheral nerves.

As used herein, the term "peripheral nerve" refers a neuron or a bundle of neurons comprising a part of the peripheral nervous system. The nervous system comprises two general components, the central nervous system, which is composed of the brain and the spinal cord, and the peripheral nervous system, which is composed of ganglia or dorsal root ganglia and the peripheral nerves that lie outside the brain and the spinal cord. One of skill in the art realizes that the nervous system may be separated anatomically, but functionally they are interconnected and interactive. The peripheral nervous system is divided into the autonomic system (parasympathetic and sympathetic), the somatic system and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

As used herein, the term "somatosensory system" refers to the peripheral nervous system division comprising primarily afferent somatic sensory neurons and afferent visceral sensory neurons that receive sensory information from skin and deep tissue, including the 12 cranial and 21 spinal nerves.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein, the term "stimulate" or "stimulation" refers to electrical, chemical, and/or magnetic stimulation that modulates the predetermined sites in the brain.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Auditory Pathways

The auditory system comprises components that convert sound pressure waves into neural impulses that are ultimately processed by the nervous system. A simplified version of these components as they appear in humans is shown in FIG. 1B. Auditory canal 101 channels pressure waves to tympanic membrane 102 which moves in response to incoming waves. Movement of the tympanic membrane 102 is transmitted to three ossicles 103 located in the middle ear. The ossicles 103 amplify the movement of the tympanic membrane 102 so that sound vibrations are converted to high pressure sound waves in fluid located in the cochlea 104. In vivo, the cochlea 104 is coiled like a snail shell.

Figure 1B:
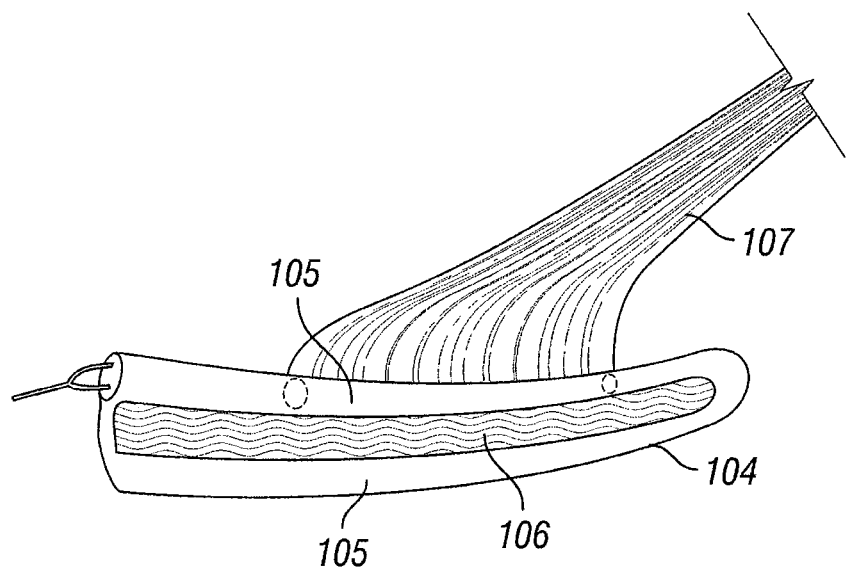

FIG. 1B shows the cochlea 104 of FIG. 1A as it would appear uncoiled. Cochlea 104 is divided into two fluid-filled chambers separated by the organ of Corti 106. Vibrations in the fluid cause mechanical stimulation of sensory receptor cells known as hair cells on the organ of Corti 106. This mechanical stimulation causes ion channels on the hair cells to open, altering their membrane potential and changing the release rate of a synaptic neurotransmitter. Afferent nerve fibers from the auditory nerve 107 take up the neurotransmitter and an action potential in the nerve fibers may be generated depending on the quantity of released neurotransmitter. This is a simplified diagram, and other afferent and efferent nerve fibers are also involved in auditory information collection and processing.

Figure 2:
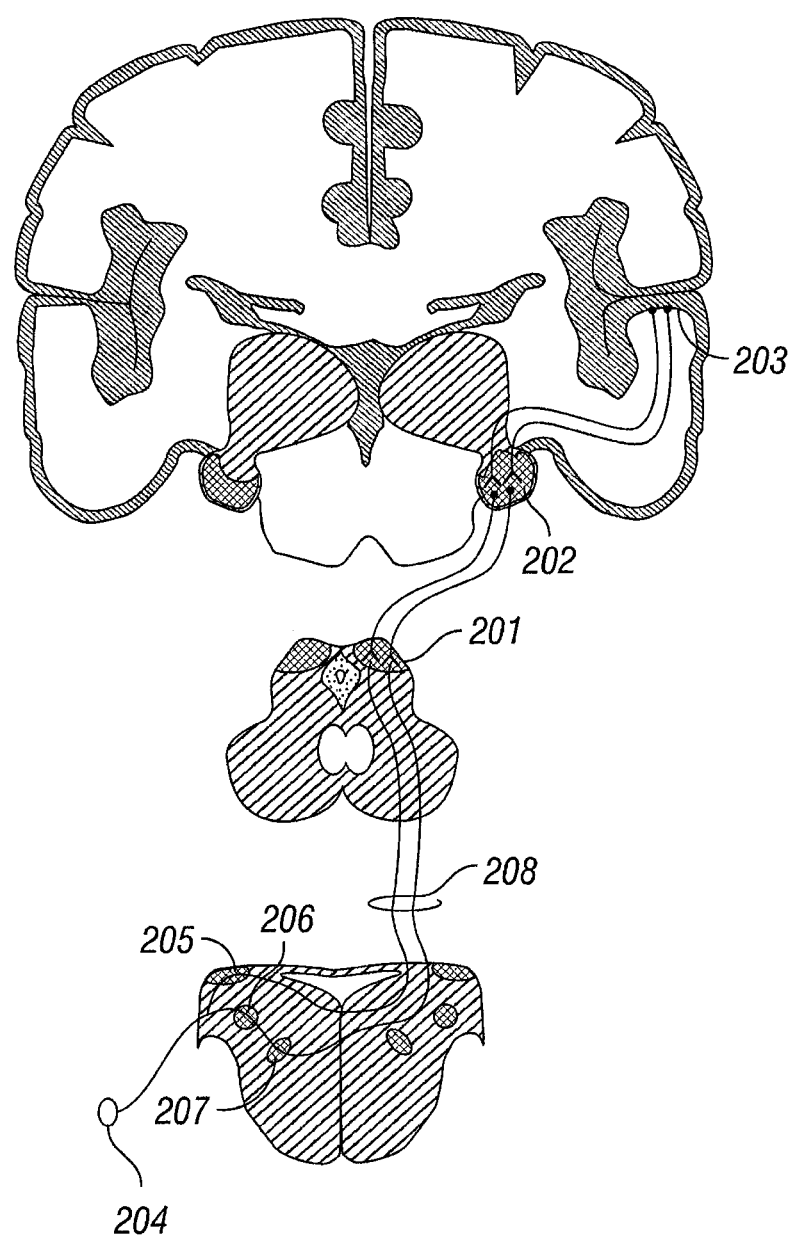
FIG. 2 is an illustration of connections in the lemniscal auditory pathway.

The auditory nerve connects to two separate pathways after leaving the cochlea. The lemniscal pathway, also known as the classical or specific auditory pathway, is the route taken for signals that humans consciously perceive as sound information. The lemniscal is phylogenetically the youngest of the two pathways. The lemniscal pathway is organized tonotopically, with specific parts of the pathway carrying information specific to received auditory frequencies. It is also linear, such that the impulse rate of lemniscal neurons is related to the amplitude of sound waves detected at the cochlea. The lemniscal pathway is illustrated in simplified form in FIG. 2. Generally, axons carrying impulses from the cochlea connect to the inferior colliculus 201 and the medial geniculate body 202 in the thalamus to the auditory cortex 203. Specifically, primary axons in synaptic contact with the hair cells of the organ of Corti (106 in FIG. 1A) have their cell bodies in the spiral ganglion 204 and enter the brainstem at the juncture of the pons and cerebellum. Here, each axon bifurcates and synapses in the dorsal and ventral cochlear nuclei 205, 206 of the medulla. Second order axons from the dorsal and ventral cochlear nuclei 205, 206 may synapse in the superior olive 207 or may pass directly to the nucleus of the inferior colliculus 201 via the lateral leminiscus 208. These connections may be made both ipsilaterally (not shown) and contralaterally.

The second pathway connected to by the auditory nerve is the extralemniscal pathway. This pathway is also known as the non-classical, nonspecific, polysensory, or diffuse auditory pathway, and is used for autonomous reactions to auditory stimuli. Moller and Rollins have found evidence suggesting that this pathway may also be used for hearing in children. The extralemniscal pathway is phylogenetically older than the lemniscal system. Because it is used for autonomous reactions, it is a faster transmission path and is also nontonotopic and non-linear. Cells of the extralemniscal pathway fire in burst mode and have a slow spontaneous firing rate relative to the lemniscal pathway cells. The auditory extralemniscal pathway makes connections with the somatosensory system at the dorsal cochlear nucleus and the inferior colliculus. Extralemniscal connections at the inferior colliculus occur at the external nucleus and the dorsal cortex. These ascending pathways then connect at all divisions of the medial geniculate bodies, the posterior intralaminar complex, and suprageniculate nuclei at the level of the superior colliculus. Afferent dorsal column neurons connect with the extralemniscal pathway at the external nucleus and the dorsal cortex. Dorsal column neurons may also connect directly with other auditory neurons such as, for example, those in the cochlear nucleus. Peripheral nerve bodies located in the dorsal root ganglia connect to the dorsal column via axonal extensions that may ascend directly to the brain or brain stem, or may connect to ascending pathways via synaptic connections in the spinal cord.

Connections from the somatosensory system to the auditory system have been explored in the past. Information from the different sensory modalities (sight, hearing, touch, etc.) is known to integrate in most higher organisms, and occurs in the human nervous system. Co-existing cutaneous and auditory responses in neuronal tissue have been observed in the caudomedial auditory cortex, adjacent to the primary auditory cortex (Fu et al., Foxe et al.).

There are also connections between the trigeminal system and the ventral cochlear nucleus. The dorsal cochlear nucleus receives input from the dorsal column (proprioception) nuclei and the ventral cochlear nucleus from the trigeminal ganglion (Shore, Vass et al. 2000; Shore, El Kashlan et al. 2003; Weinberg and Rustioni 1987). The trigeminal ganglion also connects to the superior olivary nucleus (Shore, Vass et al. 2000). Electrical stimulation of the somatosensory trigeminal ganglion can influence the activity of central auditory neurons in a manner distinct from acoustic stimulation, suggesting activation of non-classical auditory pathways (El-Kashlan and Shore 2004). Furthermore, the activation seems to be predominantly ipsilateral (El-Kashlan and Shore 2004). These connections may be involved in generating or modulating perceptions of phantom sounds which can be modified by manipulations of somatic regions of the head and neck ("somatic tinnitus")(Levine, Abel et al. 2003; Shore, El Kashlan et al. 2003). Also, C2 (occipital and greater auricular nerve) innervates the dorsal cochlear nucleus (Kanold and Young 2001) as well as the rest of the body via the cuneate nucleus of the dorsal column (Itoh, Kamiya et al. 1987; Wright and Ryugo 1996).

Thus, it is envisioned that stimulation of the somatosensory system can treat auditory dysfunction, for example, tinnitus by activation of the extralemniscal auditory connections to the somatosensory system.

III. Electrical Stimulation Devices

Figure 3A:
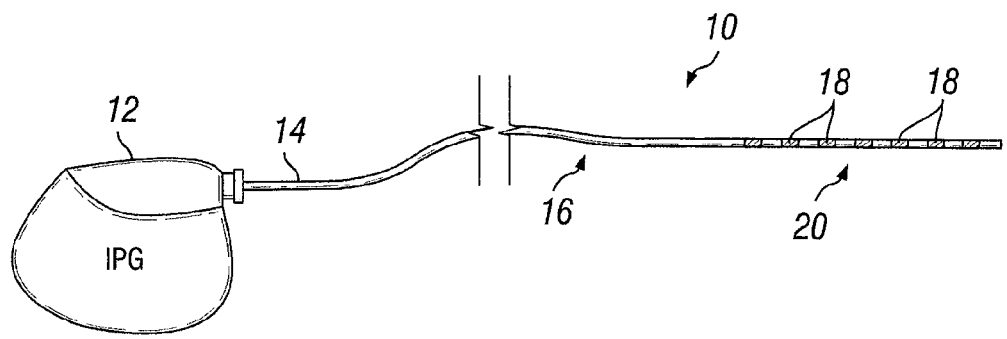
FIGS. 3A-3B illustrate example stimulation systems for electrically stimulating peripheral nerves.
Figure 3B:
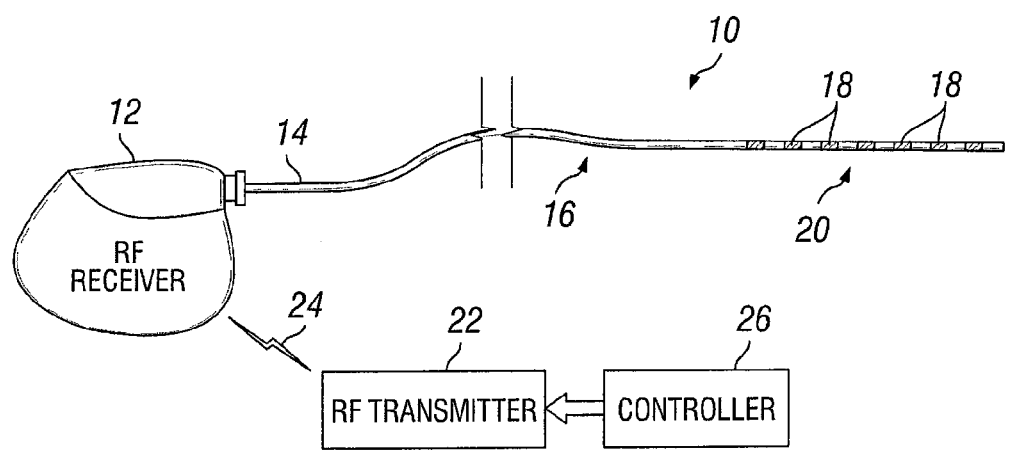

FIGS. 3A-3B illustrate example neurological stimulation systems 10 for electrically stimulating a predetermined site, for example, a peripheral nerve, to treat auditory dysfunction. In general terms, stimulation system 10 includes an implantable electrical stimulation source 12 and one or more implantable electrical stimulation leads 14 for applying electrical stimulation pulses to a predetermined site. In operation, one or both of these primary components are implanted in or on a subject's body, as discussed below. In certain embodiments, stimulation source 12 is coupled directly to a connecting portion 16 of stimulation lead 14. In certain other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site, according to suitable stimulation parameters (e.g., duration, amplitude or intensity, frequency, pulse width, etc.). One example of stimulation parameters used to treat an auditory dysfunction, such as, for example, tinnitus uses an amplitude in the range of about 2 mA to about 100 mA, a frequency in the range of about 3 Hz to about 80 Hz, and a pulse width in the range of about 5 microseconds to about 100 microseconds.

The predetermined site in communication with the stimulation lead 14 is a peripheral nerve in a preferred embodiment. Peripheral nerves can include cranial nerves for example, olfactory nerve, optic nerve, oculomotor nerve, trochlear nerve, trigeminal nerve, abducens nerve, facial nerve, vestibulocochlear (auditory) nerve, glossopharyngeal nerve, vagal nerve, accessory nerve, and the hypoglossal nerve. In addition to cranial nerves, the predetermined site can be a dermatome area, for example, C2, C3, C4, C5, C6, C7, C8, as well as any thoracic, lumbar or sacral dermatome. Other dermatomes that can be included in the present invention include dermatomes associated with cranial nerves having somatosensory function, for example, but not limited to dermatomes associated with the trigeminal nerve, intermediate part of the facial nerve, glossopharyngeal nerve, or vagal nerve. Peripheral nerves also includes spinal nerves, which in general, spinal nerves are named after the vertebral segment of the spinal column above their origin. For example, the spinal nerve originating under the third thoracic vertebra may be termed the third thoracic nerve. Thus, spinal nerves can include, but are limited to cervical nerve roots (e.g., C1, C2, C3, C4, C5, C6, C7 and C8), thoracic nerve roots (e.g., T1, T2, T3, T4, T5, T6, T7, T8, T9, T10, TI 1, T12), lumbar nerve roots (L1, L2, L3, L4, L5) sacral nerve roots (e.g., S1, S2, S3, S4, S5) and the coccygeal nerve. Other peripheral nerves are spinal nerves such as the suboccipital nerve, the greater occipital nerve, the lesser occipital nerve, the greater auricular nerve, the lesser auricular nerve, the phrenic nerve, and the brachial plexus, which branches to form the dorsal scapular nerve, the thoracic nerve, the suprascapular nerve, the lateral pectoral, the musculocutaneous nerve, the axillarily nerve, the radial nerve, the median nerve, the ulnar nerve, the intercostal nerves, and other minor peripheral nerves, as well as parasympathetic and/or sympathetic nerves. In certain embodiments, the peripheral nerve stimulated is the trigeminal nerve or the trigeminal dermatome or any peripheral nerve associated with the C2 dermatome area, C3 dermatome area, cranial nerves, the median nerve or any combination thereof. Peripheral nerve ganglia, which are collections of peripheral nerve cell bodies, are predetermined sites in communication with stimulation lead 14 in certain embodiments. A doctor, the patient, or another user of stimulation source 12 may directly or indirectly input stimulation parameters to specify or modify the nature of the stimulation provided. In certain embodiments, transcutaneous implantation of stimulation lead 14 is used either permanently or temporarily.

Some embodiments employ a burst stimulus. Examples of burst stimulus are found in U.S. Application entitled "New Stimulation Design for Neuromodulation", filed Oct. 20, 2005, and incorporated herein by reference. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, about 10 milliseconds to about 300 milliseconds, or any range therebetween. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

In one embodiment, as shown in FIG. 3A, stimulation source 12 includes an implantable pulse generator (IPG). An exemplary IPG may be one incorporated in the Genesis® System manufactured by Advanced Neuromodulation Systems, Inc., part numbers 3604, 3608, 3609, and 3644. In another embodiment, as shown in FIG. 3B, stimulation source 12 includes an implantable wireless receiver. An example wireless receiver may be one incorporated in the Renew® System manufactured by Advanced Neuromodulation Systems, Inc., part numbers 3408 and 3416. In another embodiment, the IPG can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. In some embodiments, the receiver may be stand-alone and no external controller 26 is required. The wireless signals are represented in FIG. 3B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the stimulation parameters of stimulation pulses transmitted through stimulation lead 14 to the predetermined peripheral nerve. Thus, the external controller 26 can be for example, a handheld programmer, to provide a means for programming the IPG. An example wireless transmitter 122 may be one manufactured by Advanced Neuromodulation Systems, Inc., such as the Renew® System, part numbers 3508 and 3516.

Conventional neuromodulation devices can be modified to apply burst stimulation to nerve tissue of a patient by modifying the software instructions stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

These conventional neuromodulation devices can be adapted by programming the microprocessor to deliver a number of spikes (relatively short pulse width pulses) that are separated by an appropriate inter-spike interval. Thereafter, the programming of the microprocessor causes the pulse generation module to cease pulse generation operations for an inter-burst interval. The programming of the microprocessor also causes a repetition of the spike generation and cessation of operations for a predetermined number of times. After the predetermined number of repetitions have been completed, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the inter-spike interval, the inter-burst interval, the number of bursts to be repeated in succession, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In another embodiment, a neuromodulation device can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

FIGS. 4A-4I illustrate example stimulation leads 14 that may be used for electrically stimulating a predetermined peripheral nerve for treating auditory dysfunction. As described above, each of the one or more stimulation leads 14 incorporated in stimulation system 10 includes one or more stimulation electrodes 18 adapted to be positioned in communication with the predetermined peripheral nerve and used to deliver to the stimulation pulses received from stimulation source 12. A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, stimulation leads 14 may be used alone or in combination. For example, unilateral stimulation of a peripheral nerve may be accomplished using a single electrical stimulation lead 14 implanted in communication with the nerve on one side of the subject's body, while bilateral electrical stimulation of the peripheral nerve may be accomplished using two stimulation leads 14 implanted in communication with the peripheral nerve on both sides of the subject's body. Multi-nerve implantation of stimulation leads can be used.

In one embodiment, the stimulation source is transcutaneously in communication with the electrical stimulation lead. In "transcutaneous", electrical nerve stimulation (TENS) the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

In addition to electrical stimulation, other forms of stimulation can be used, for example magnetic. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Quick pulses of magnetic stimulation can be applied externally or transcranially, for example repetitive transcranially magnetic stimulation (rTMS).

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc.

The preferred neurostimulation devices should allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

IV. Implantation of Electrical Devices

Figure 5:
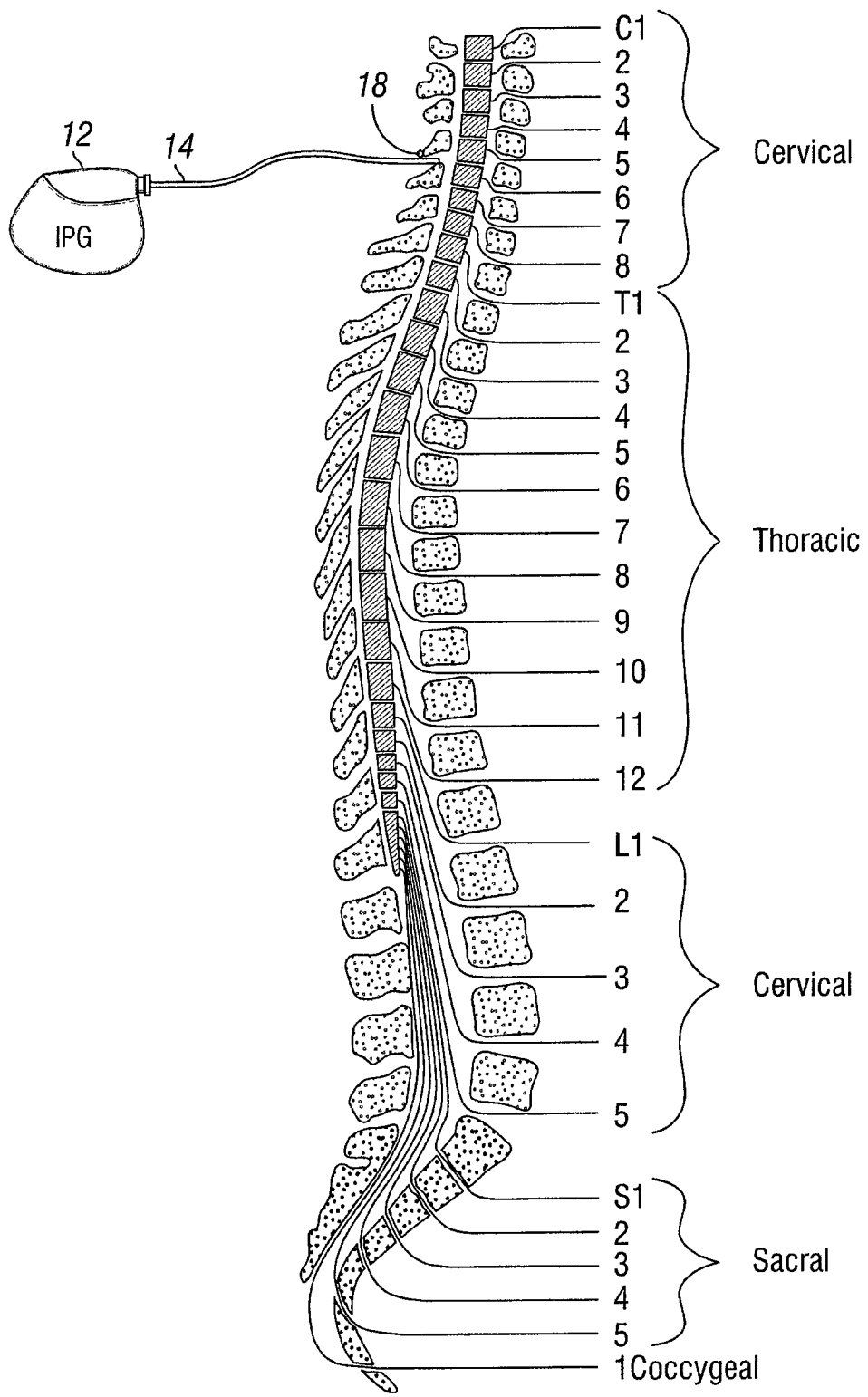
FIG. 5 illustrates implantation of a single stimulation lead near the spinal cord to stimulate a peripheral nerve.

FIG. 5 illustrates example placement of a single stimulation lead 14 for medial electrical stimulation of a peripheral nerve dorsal root ganglia by a stimulation electrode 18. Those of skill in the art are aware that the peripheral nerves can be stimulated anywhere along the nerve. Thus, it is not necessary to stimulate the dorsal root ganglia. Multiple stimulation leads 14 and electrodes 18 are used in other embodiments of the invention.

Figure 6:
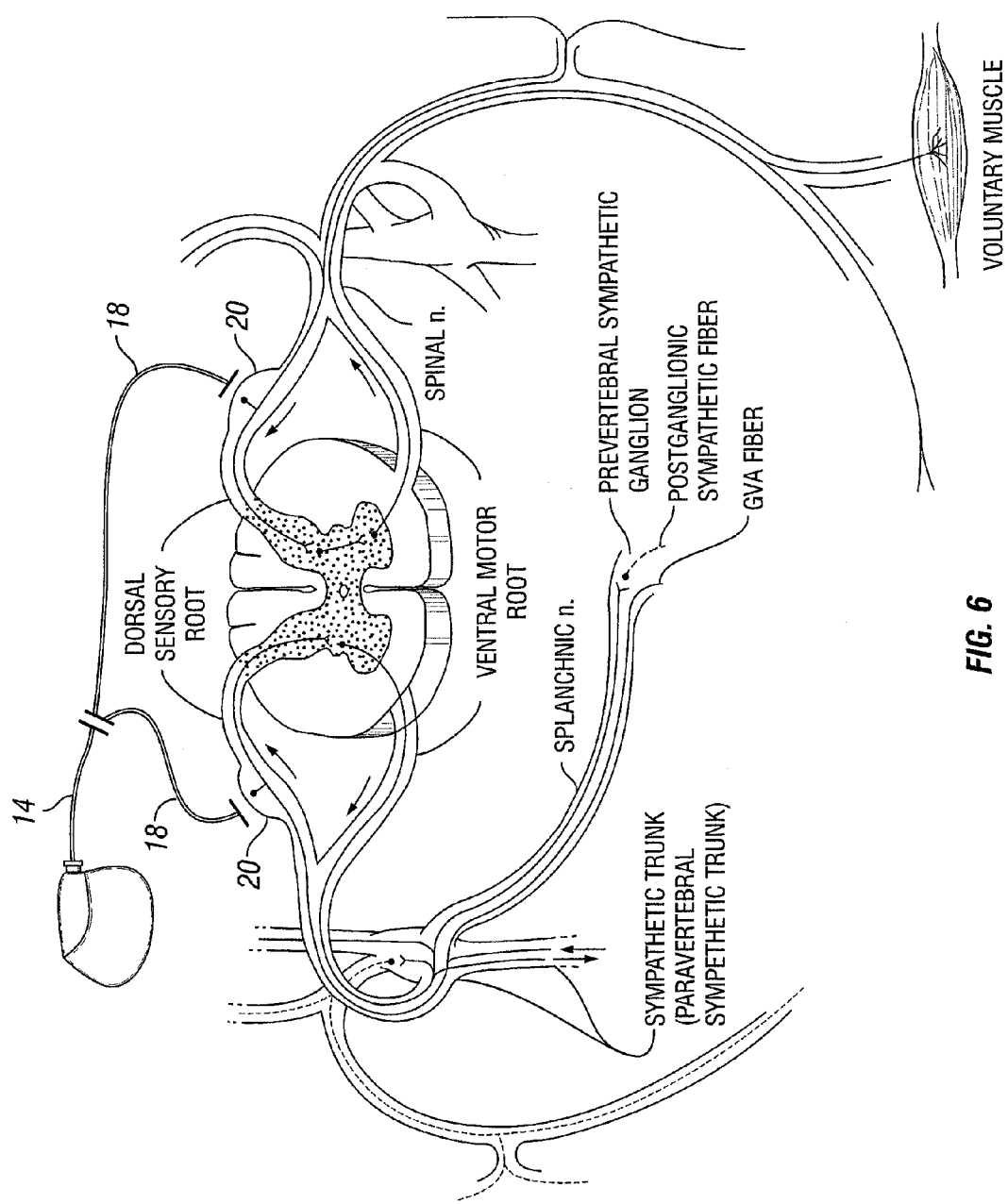
FIG. 6 illustrates an example method of implanting the stimulation system of FIGS. 1A-1B with bilateral leads in communication with peripheral nerves.

FIG. 6 is an illustration of an implantable pulse generator with a single simulation lead 14 that is employed with two stimulation electrodes 18 for bilateral stimulation of peripheral nerve dorsal root ganglia 20. As indicated above, those of skill in the art realize that the peripheral nerve can be stimulated anywhere along the nerve.

Figure 8:
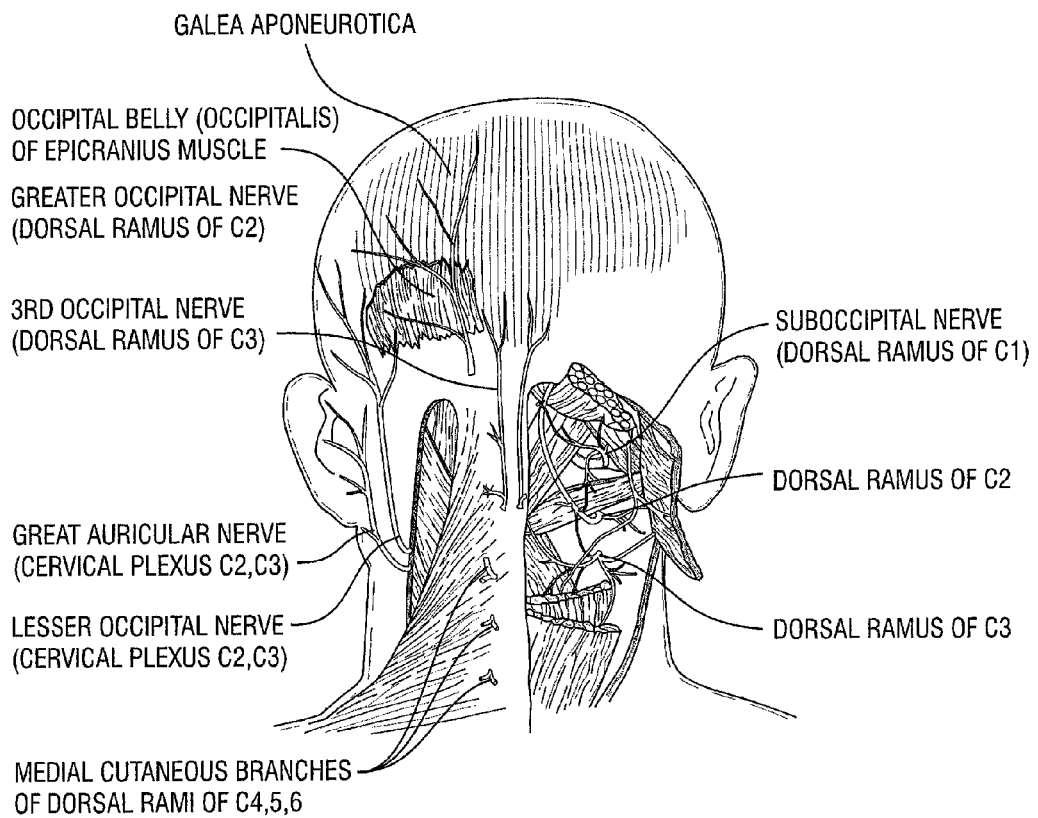
FIG. 8 shows the anatomy of the occiput or occipital area of a subject's head. Anatomical structures shown include nerves, muscle and the galea.

FIG. 4 illustrate examples of one or more stimulation leads 14 implanted subcutaneously such that one or more stimulation electrodes 18 of each stimulation lead 14 are positioned in communication with the a dermatome (e.g., C2-C8, T1-T12, L1-L5, S1-S5), cervical nerve roots (e.g., C1, C2, C3, C4, C5, C6, C7 and C8) cranial nerves (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and hypoglossal nerve), thoracic nerve roots (e.g., T1, T2, T3, T4, T5, T6, T7, T8, T9, T10, T11, T12), lumbar nerve roots (e.g., L1, L2, L3, L4, L5), sacral nerve roots (S1, S2, S3, S4, S5), as well as any other spinal or peripheral nerve. Other dermatomes that can be included in the present invention include dermatomes associated with cranial nerves having somatosensory function, for example, but not limited to dermatomes associated with the trigeminal nerve, intermediate part of the facial nerve, glossopharyngeal nerve, or vagal nerve. FIGS. 7 and 8 illustrate example placement of a single stimulation lead 14 for medial electrical stimulation of a dermatome area. FIG. 8 illustrates example placement of an electrode in the occipital area or C2/C3 dermatome area. In certain embodiments one or more stimulation electrodes 18 are positioned in the C2 dermatome area, subcutaneously, but superior to the galea. Within certain areas of the C2 dermatome area, there is little or no muscle, this area primarily consists of fat, fascia, periostium, and neurovascular structures (e.g., galea). Thus, the advantage implanting a stimulation lead in this area is that there will be no to little muscular contraction. One of skill in the art is aware that stimulation of the C2 dermatome area may result in stimulation of various neuronal structures, for example, but not limited to the C2 dermatome area, C3 dermatome, trigeminal dermatome, trigeminal nerve, olfactory nerve, other cranial nerves, or other cervical nerve roots.

Different numbers of stimulation leads 14 and stimulation electrodes 18 may be used in other embodiments of the invention. Additionally, other peripheral nerves or peripheral nerve branches are stimulated by stimulation electrodes 18 in certain embodiments.

Figure 9:
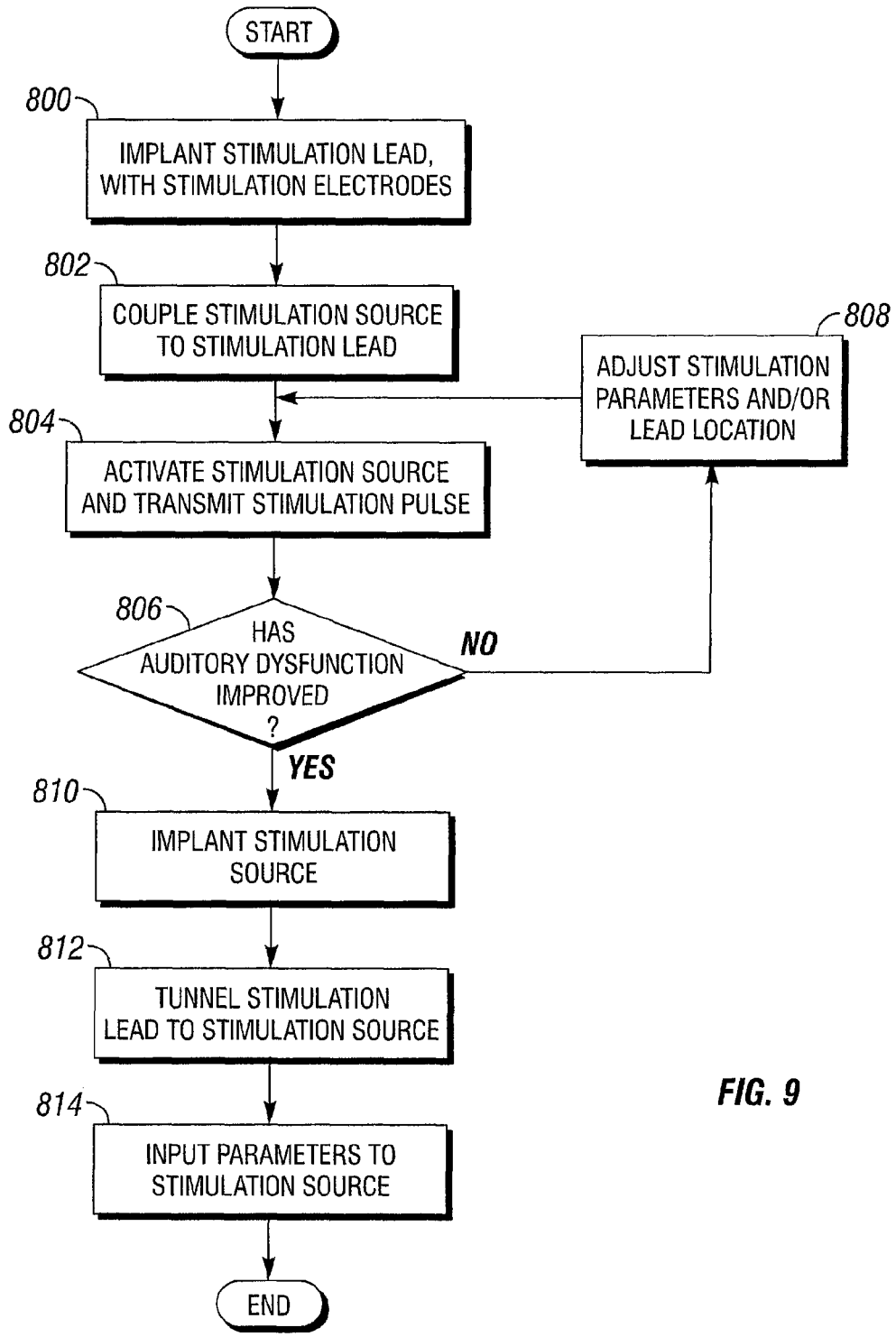
FIG. 9 is a block diagram of processes according to a method for treating auditory dysfunctions such as tinnitus using a peripheral nerve stimulation system.

FIG. 9 illustrates an example method of treating auditory dysfunction using stimulation system 10, described above, implanted into a person's body with stimulation lead 14 located in communication with a peripheral nerve for treating auditory dysfunction. At process 800, one or more stimulation leads 14 are implanted such that one or more stimulation electrodes 18 of each stimulation lead 14 are positioned in communication with a peripheral nerve (for the purposes described herein and as those skilled in the art will recognize, when an embedded stimulation system, such as the Bion®, is used, it is positioned similar to positioning the lead 14). Techniques for implanting stimulation leads such as stimulation lead 14 are known to those skilled in the art. In certain embodiments, as described above, one or more stimulation electrodes 18 are positioned in communication with a peripheral nerve. Stimulation electrodes 18 are commonly positioned in communication with the peripheral nerve by electrodes applied cutaneously to the dermatome area of a peripheral nerve. Stimulation electrodes 18 can also be positioned subcutaneously in communication with the peripheral nerve or on the nerve root ganglion. The electrodes are carried by two primary vehicles: percutaneous leads and a laminotomy lead. Percutaneous leads commonly have two or more, equally-spaced electrodes, which are placed subcutaneously in communication with the peripheral nerve. For unilateral auditory dysfunction, percutaneous leads are positioned on the peripheral nerve on the contralateral side of the body corresponding to the "afflicted" side of the body, and for bilateral auditory dysfunction, a single percutaneous lead with two or more leads is positioned with each lead in communication with a peripheral nerve. An example of an eight-electrode percutaneous lead is an OCTRODE® lead manufactured by Advanced Neuromodulation Systems, Inc. Use of a Bion® stimulation system manufactured by Advanced Bionics Corporation is also contemplated in certain embodiments.

Figure 4A:
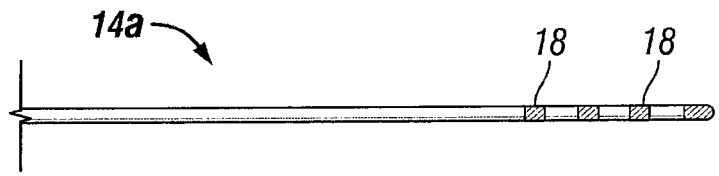
FIGS. 4A-4I illustrate example electrical stimulation leads that may be used to electrically stimulate peripheral nerves.
Figure 4B:
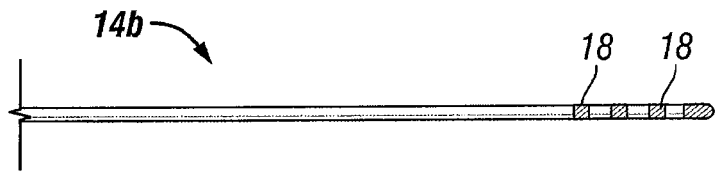
Figure 4C:
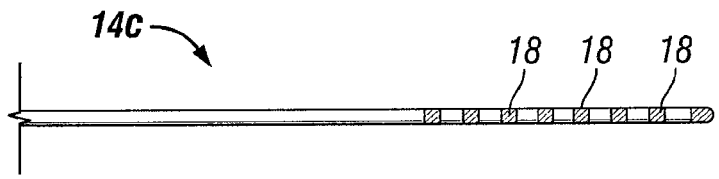
Figure 4D:
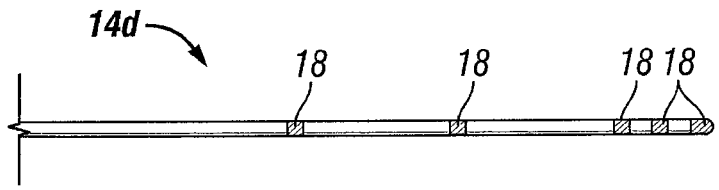
Figure 4E:
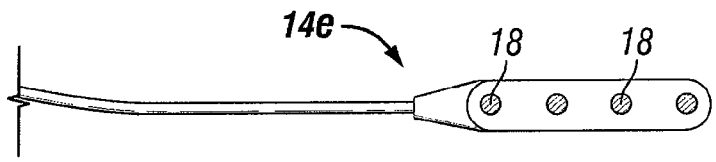
Figure 4F:
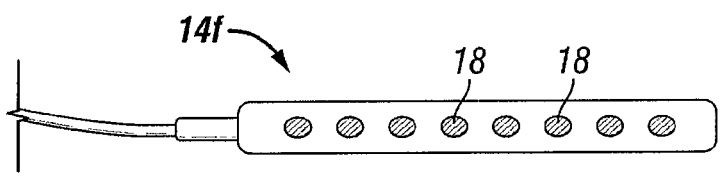
Figure 4G:
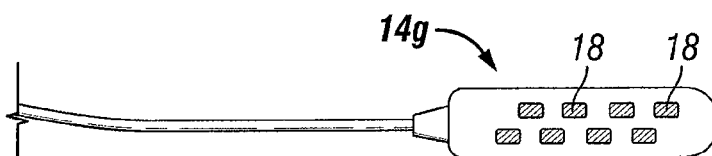
Figure 4H:
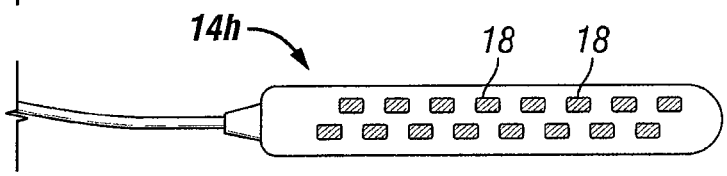
Figure 4I:
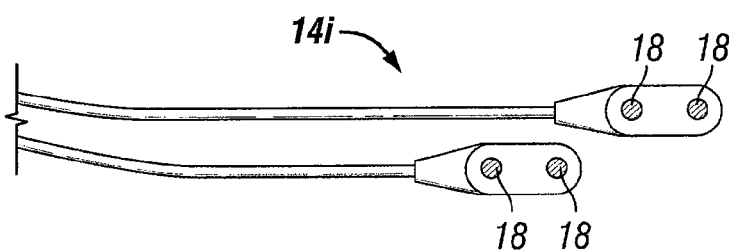

In contrast to the percutaneous leads, laminotomy leads have a paddle configuration and typically possess a plurality of electrodes (for example, two, four, eight, or sixteen) arranged in one or more columns. An example of a sixteen-electrode laminotomy lead is shown in FIG. 4H. Another example of a laminotomy lead is an eight-electrode, two column laminotomy lead called the LAMITRODE® 44, which is manufactured by Advanced Neuromodulation Systems, Inc. Implanted laminotomy leads are commonly transversely centered over the physiological midline of a patient. In such position, multiple columns of electrodes are well suited to address bilateral auditory dysfunction, where electrical energy may be administered bilaterally near peripheral nerve ganglia around the spinal cord via a single laminotomy lead. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to properly position the laminotomy lead. The laminotomy lead offers a more stable platform, which is further capable of being sutured in place, that tends to migrate less in the operating environment of the human body. Depending on the position of insertion, however, access to the peripheral nerve or nerve ganglia may only require a partial removal of the ligamentum flavum at the insertion site. In some embodiments, two or more laminotomy leads may be positioned to treat multiple peripheral nerves or multiple branch points of a single nerve.

In addition to stimulation of peripheral nerve ganglia, the laminotomy or percutaneous leads can be implanted subcutaneously in the dermatome area as shown in FIGS. 7 and 8 to stimulate any cranial and/or cervical nerve root associated with the C2 dermatome area. The leads can also be implanted subcutaneously at other dermatomes such as C3, trigeminal nerve dermatome, etc.

At process 802, if necessary, stimulation source 12 may be coupled directly to connecting portion 16 of stimulation lead 14. Alternatively, as described above and if necessary, stimulation source 12 may not be coupled directly to stimulation lead 14 and may instead be coupled to stimulation lead 14 via an appropriate wireless link. Of course, as those skilled in the art know, an embedded stimulation system will not need to be so coupled.

Intra-implantation trial stimulation may be conducted at processes 804 through 808. These processes may be used to optimize the effect of the treatment on auditory dysfunction. In certain embodiments, the intra-implantation trial stimulation is not performed, and the method proceeds from process 802 to 810. At process 804, stimulation source 12 is activated to generate and transmit stimulation pulses via one or more stimulation electrodes 18. At process 806, informal subjective questioning of the person, formal subjective testing and analysis according to one or more audiology tests and/or other analyses (such as the Goebel tinnitus questionnaire or other validated tinnitus questionnaires, audiometry, tinnitus matching, impedance, BAEP, and OAE) may be performed to determine whether the subject's auditory dysfunction has sufficiently improved through the intra-implantation trial stimulation. If the subject's auditory dysfunction has not sufficiently improved, one or more stimulation parameters may be adjusted, stimulation lead 14 may be moved incrementally or even re-implanted, or both of these modifications may be made at process 808 and the trial stimulation and analysis repeated until the auditory dysfunction has sufficiently improved. Once the stimulation parameters have been properly set and stimulation lead 14 has been properly positioned such that subject's auditory dysfunction has improved, intra-implantation trial stimulation is complete. One of skill in the art is aware that other types of intra-implantation trailing methods or stimulation trails can be used in the present invention, for example, but not limited to transcutaneous electrical nerve stimulation (TENS), transmagnetic stimulation (TMS), nerve blocks, etc.

Once stimulation lead 14 has been properly implanted and secured, and any trial stimulation completed, if necessary, stimulation source 12 is implanted at process 810. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the lower back or buttocks. Where stimulation lead 14 includes connecting portion 16, connecting portion 16 may be tunneled, at least in part, subcutaneously to the implant site of stimulation source 12 at process 812. Some embodiments of the invention may use a non-implantable stimulation source. At process 814, a doctor, the patient, or another user of stimulation source 12 may directly or indirectly input stimulation parameters for controlling the nature of the electrical stimulation provided to the peripheral nerve, if not already set during any intra-implantation trial stimulation period. Where appropriate, post-implantation trial stimulation may be conducted, over one or more weeks or months for example, and any necessary modifications made accordingly.

Although example processes are illustrated and described, the present invention contemplates two or more processes taking place substantially simultaneously or in a different order. In addition, the present invention contemplates using methods with additional processes, fewer processes, or different processes, so long as the processes remain appropriate for implanting stimulation system 10 into a person for electrical stimulation of the predetermined site, such as, for example the C2 dermatome area, C3 dermatome area, a cervical (e.g., C1, C2, C3, etc) or other spinal nerve or any cranial nerve (e.g., trigeminal, olfactory, etc) to treat auditory dysfunction.

One technique that offers the ability to affect neuronal function is the delivery of electrical stimulation for neuromodulation directly to target tissues via an implanted device having a probe. The probe is a stimulation lead or electrode in certain embodiments. The electrode assembly may be one electrode, multiple electrodes, or an array of electrodes in or around the target area. The proximal end of the probe is coupled to system to operate the device to stimulate the target site. Thus, the probe is coupled to an electrical signal source which, in turn, is operated to stimulate the predetermined treatment site.

V. Infusion Pumps

In further embodiments, it may be desirable to use a drug delivery system independently or in combination with electrical stimulation to result in the stimulation parameters of the present invention. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Implantable infusion pumps are used with certain embodiments of the invention to provide chemical stimulation. Further details of implantable infusion pumps that may be used with the invention are found in pending U.S. application Ser. No. 10/755,985 "Actuation System and Method for an Implantable Infusion Pump" herein incorporated by reference.

In further embodiments, "active pumping" devices or so-called peristaltic pumps can be used as described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 all of which are incorporated by reference in their entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

Instances in which chemical and electrical stimulation will be administered to the subject, a catheter having electrical leads may be used, similar to the ones described in U.S. Pat. Nos. 6,176,242; 5,423,877; 5,458,631 and 5,119,832, each of which are incorporated herein by reference in its entirety.

Still further, the present invention can comprise a chemical stimulation system that comprises a system to control release of neurotransmitters (e.g., glutamate, acetylcholine, norepinephrine, epinephrine), chemicals (e.g., zinc, magnesium, lithium) and/or pharmaceuticals that are known to alter the activity of neuronal tissue. For example, infusion formulation delivery system can utilize a control system having an input-response relationship. A sensor generates a sensor signal representative of a system parameter input (such as levels of neurotransmitters), and provides the sensor signal to a controller. The controller receives the sensor signal and generates commands that are communicated to the infusion formulation delivery device. The infusion formulation delivery device then delivers the infusion formulation output to the predetermined site at a determined rate and amount in order to control the system parameter.

Sensor may comprise a sensor, sensor electrical components for providing power to the sensor and generating the sensor signal, a sensor communication system for carrying the sensor signal to controller, and a sensor housing for enclosing the electrical components and the communication system. Controller may include one or more programmable processors, logic circuits, or other hardware, firmware or software components configured for implementing the control functions described herein, a controller communication system for receiving the sensor signal from the sensor, and a controller housing for enclosing the controller communication system and the one or more programmable processors, logic circuits, or other hardware, firmware or software components. The infusion formulation delivery device may include a suitable infusion pump, infusion pump electrical components for powering and activating the infusion pump, an infusion pump communication system for receiving commands from the controller, and an infusion pump housing for enclosing the infusion pump, infusion pump electrical components, and infusion pump communication system. Such systems are described in U.S. Pat. No. 6,740,072, which is incorporated herein by reference in its entirety.

In certain embodiments, the sensor can be an electrode that senses a hyperactive burst pattern of activity, which in turns stimulates the infusion pump to release a chemical or stimulating drug or agent to modify the neuronal activity. The chemical or stimulating agent can be either an inhibiting agent or stimulating agent.

Herein, stimulating drugs comprise medications, anesthetic agents, synthetic or natural peptides or hormones, neurotransmitters, cytokines and other intracellular and intercellular chemical signals and messengers, other agents such as zinc and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts, anesthetics (e.g., lidocane), and magnesium may also be used in combination with electrical stimulation.

VI. Treatment of Auditory Dysfunction

The present method acts to stimulate nerve afferents which in turn stimulate the brain and cause/allow the brain to act in the best interest of the host through use of the brain's natural mechanisms. The prior art fails to recognize that stimulation of a patient's peripheral nerves can provide the therapeutic treatments for auditory dysfunction according to the instant invention.

The present invention is particularly useful in the treatment of auditory dysfunction in humans. However, one skilled in the art appreciates that the present invention is applicable to other animals which experience auditory dysfunction. This may include, for example, primates, canines, felines, horses, elephants, dolphins, etc. Utilizing the various embodiments of the present invention, one skilled in the art may be able to modulate the auditory system via peripheral nerve stimulation to achieve a desirable result.

One technique that offers the ability to affect neuronal function is the delivery of electrical, chemical, and/or magnetic stimulation for neuromodulation directly to target tissues via an implanted device having a probe. The probe is, for example, a stimulation lead, electrode assembly, or a catheter in certain embodiments of the invention. An electrode assembly may be one electrode, multiple electrodes, or an array of electrodes in or around the target area. The proximal end of the probe is coupled to system to operate the device to stimulate the target site. Thus, the probe is coupled to an electrical signal source, which, in turn, is operated to stimulate the predetermined treatment site of a peripheral nerve or nerves. In the case of unilateral auditory dysfunction, contralateral peripheral nerve stimulation may be more effective than ipsilateral stimulation. However, as the auditory system crosses over at numerous points, effective auditory dysfunction treatment may require bilateral stimulation. Stimulation of the predetermined site is performed to modulate neuronal extralemniscal pathways of the auditory system. Modulation of this neuronal tissue may result in efficacious treatment of auditory dysfunction in a subject. While optimal results from the treatment may result in the complete cessation of auditory dysfunction in a subject, any lessening of the amplitude of a subject's auditory dysfunction may be considered successful according to the present invention.

The predetermined site can be, for example, but not limited to a dermatome area, for example, C2, C3, C4, C5, C6, C7, C8, as well as any thoracic, lumbar or sacral dermatome. Cervical nerve roots (e.g., C1, C2, C3, C4, C5, C6, C7 and C8) and cranial nerves (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and hypoglossal nerve) to provide therapeutic treatments according to the instant invention. Other dermatomes that can be included in the present invention include dermatomes associated with cranial nerves having somatosensory function, for example, but not limited to dermatomes associated with the trigeminal nerve, intermediate part of the facial nerve, glossopharyngeal nerve, or vagal nerve. Other peripheral nerves are spinal nerves such as the suboccipital nerve, the greater occipital nerve, the lesser occipital nerve, the greater auricular nerve, the lesser auricular nerve, the phrenic nerve, and the brachial plexus, which branches to form the dorsal scapular nerve, the thoracic nerve, the suprascapular nerve, the lateral pectoral, the musculocutaneous nerve, the axillarily nerve, the radial nerve, the median nerve, the ulnar nerve, and other minor peripheral nerves, as well as sympathetic and parasympathetic nerves. Yet further, other peripheral nerves also includes thoracic nerve roots (e.g., T1, T2, T3, T4, T5, T6, T7, T8, T9, T10, T11, T12), lumbar nerve roots (L1, L2, L3, L4, L5) sacral nerve roots (e.g., S1, S2, S3, S4, S5) and the coccygeal nerve.

One example of stimulation parameters that can be used in the present invention is a parameter set with an amplitude in the range of about 2 mA to about 100 mA, a frequency in the range of about 1 Hz to about 80 Hz, and a pulse width in the range of about 5 microseconds to about 100 microseconds.

One of skill in the art is aware that stimulation parameters can be varied to achieve the desired result. One such parameter that may be varied in the present invention is signal frequency. Altering the frequency signal can result in the generation of a bursting type rhythm or burst stimulus frequency or burst mode stimulation, as described in "New Stimulation Design for Neuromodulation", filed Oct. 20, 2005 incorporated by reference herein.

In certain embodiments, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. One skilled in the art will further realize that each burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. One of skill in the art is aware that the frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween. The burst stimulus is followed by an inter-burst interval a duration in the range of about 5 milliseconds to about 5 seconds, preferably, about 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz,), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

In the auditory system, tonic firing the contents of auditory information, while burst firing may transmit the change in the auditory environment and valence or importance attached to that sound (Lisman 1997; Sherman 2001; Swadlow and Gusev 2001). Repetitive stimulus presentation results in decreased neuronal response to that stimulus, known as auditory habituation at the single cell level (Ulanovsky et al., 2003), auditory mismatch negativity at multiple cell level (Naatanen et al., 1993; Ulanovsky et al., 2003).

Many auditory dysfunctions are constantly present. For example, tinnitus is usually constantly present, e.g., a non-rational valence is attached to the internally generated sound, and there is no auditory habituation to this specific sound, at this specific frequency. Thus, tinnitus is the result of hyperactivity of lesion-edge frequencies, and auditory mismatch negativity in tinnitus patients is specific for frequencies located at the audiometrically normal lesion edge (Weisz 2004).

As pathological valence of the tinnitus sound is mediated by burst firing, burst firing is increased in tinnitus in the extralemniscal system (Chen and Jastreboff 1995; Eggermont and Kenmochi 1998; Eggermont 2003), in the inner hair cells (Puel 1995; Puel et al., 2002), the auditory nerve (Moller 1984), the dorsal and external inferior colliculus (Chen and Jastreboff 1995), the thalamus (Jeanmonod, Magnin et al., 1996) and the secondary auditory cortex (Eggermont and Kenmochi 1998; Eggermont 2003). Furthermore, quinine, known to generate tinnitus, induces an increased regularity in burst firing, at the level of the auditory cortex, inferior colliculus and frontal cortex (Gopal and Gross 2004). It is contemplated that tinnitus can only become conscious if an increased tonic firing rate is present in the lemniscal system, generating the sound. This increased firing activity has been demonstrated in the lemniscal dorsal cochlear nucleus (Kaltenbach, Godfrey et al., 1998; Zhang and Kaltenbach 1998; Kaltenbach and Afman 2000; Brozoski, Bauer et al., 2002; Zacharek et al., 2002; Kaltenbach et al., 2004), inferior colliculus (Jastreboff and Sasaki 1986; Jastreboff, Brennan et al., 1988; Jastreboff 1990) (Gerken 1996) and primary auditory cortex (Komiya, 2000). Interestingly, not only tonic firing is increased generating the tinnitus sound, but also the burst firing (Ochi and Eggermont 1997) (keeping it conscious) at a regular basis. Repetitive burst firing is known to generate tonic gamma band activity (Gray and Singer 1989; Brumberg, 2000). Thus, it is envisioned that the present invention can be used to modify burst firing, thus modifying tonic gamma activity. However, other pathways may be employed by embodiments of the invention that potentially contribute to the treatment efficacy.

Burst mode firing boosts the gain of neural signaling of important or novel events by enhancing transmitter release and enhancing dendritic depolarization, thereby increasing synaptic potentiation. Conversely, single spiking mode may be used to dampen neuronal signaling and may be associated with habituation to unimportant events (Cooper 2002). It is believed that the main problem in tinnitus is that the internally generated stimulus does not decay due to the presence of regular bursting activity telling the cortex this signal is important and has to remain conscious.

Thus, in the present invention, it is envisioned that a burst mode type stimulation can attack either of these two pathways: slowing down tonic firing in the lemniscal system (below 40 Hz) or removing the valence attached to it by the extralemniscal system by suppressing the bursting rhythm, thereby treating auditory dysfunctions such as tinnitus. Yet further, the system of the present invention can also make the auditory dysfunction disappear via auditory habituation. Suppressing the burst firing in the frontal cortex may alter the emotional effect of tinnitus, with the tinnitus persisting, but without much influence on the daily life of a tinnitus sufferer.

Thus, using the therapeutic stimulation system of the present invention, the predetermined site is stimulated in an effective amount or effective treatment regimen to decrease, reduce, modulate or abrogate the neurological disorder. Thus, a subject is administered a therapeutically effective stimulation so that the subject has an improvement in the parameters relating to tinnitus including the Goebel tinnitus questionnaire or other validated tinnitus questionnaires, audiometry, tinnitus matching, impedance, BAEP, and OAE. The improvement is any observable or measurable improvement. Thus, one of skill in the art realizes that a treatment may improve the patient condition, but may not be a complete cure of the disease.

In certain embodiments, in connection with improvement the electrical stimulation may have a "brightening" effect on the person such that the person looks better, feels better, moves better, thinks better, and otherwise experiences an overall improvement in quality of life.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the disease.

VII. Examples

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of Tinnitus

Thirteen patients with tinnitus were treated by stimulating at least one peripheral nerve. 200 Hz, 250 microsecond pulse width pulses were used with amplitude dependent on an individual threshold. Of these, four noted a decrease in tinnitus, one noted an increase and eight had no alteration in tinnitus. Tinnitus was evaluated using TMS, TENS, the Goebel tinnitus questionnaire, audiometry, tinnitus matching, impedance, BAEP, and OAE.

Example 2

Treatment of Auditory Agnosia and Tinnitus

Auditory agnosia is characterized by a relatively isolated deficit in auditory comprehension despite normal hearing.

When only verbal material is not understood, it is often called word deafness; when the deficit is in recognizing environmental sounds, it is often termed nonverbal auditory agnosia (Saygin, Dick et al. 2003).

In a patient suffering word deafness with associated complete auditory agnosia (verbal and non-verbal) and bilateral tinnitus, TENS stimulation was capable of attenuating the tinnitus and improving auditory agnosia during stimulation. In order to obtain a permanent suppression a bilateral subcutaneous occipital nerve stimulation was implanted leading to a continuous improvement of both tinnitus and auditory agnosia.

Patient History:

After a flu like syndrome a patient became comatose due to a bilateral herpes encephalitis, from which she recovered. Initially she presented with a complete cortical deafness, however after 3 to 4 weeks the patient recovered partially, with almost normalized pure tone perception, but leaving her with a complete auditory agnosia and bilateral tinnitus. Language function per se is intact, with normal language comprehension and (motor) speech, but speech comprehension is 0%. The patient can communicate via lipreading and reading. Her auditory agnosia was complete, inclusive of a pure word deafness (=auditory verbal agnosia). She does not recognize the sound of a barking dog, the sound of a car, she does not recognize the voice of her husband, she only hears sounds, perceived as a lot of chaotic noise.

Audiologic Evaluation:

Pure tone audiometry: in the right ear an average perception loss of 40 dB is noted, in the left ear an average hearing loss of 50 dB Speech audiometry: 0% for all intensities Language analysis: normal reading, writing and language testing Tinnitus Evaluation Visual Analoge Scale (intensity) rating of her tinnitus: 10/10 left side, 5/10 right side Tinnitus matching: polyphonic tinnitus centered around 250 dB, 40 dB above sensorineural hearing level. Tinnitus worsens on talking, chewing and head movement (somatic tinnitus), as well as on exertion, tinnitus improves slightly when resting. The perceived sound is described as if 10 airplanes are taking off at the same time.

Tinnitus Questionnaire (Goebel and Hiller)(grade 0-4): grade 4, i.e., a decompensated severe tinnitus.

MRI Evaluation:

MRI with and without Gadolineum demonstrates thickened meninges at the temporal lobe and contrast enhancement of the internal auditory meatus.

Functional MRI resulted in absent activation of Wernicke's area with auditory word presentation, but activation of Wernicke's area with visual word presentation.

Treatment

The patient received transcranial magnetic stimulation at 1, 5, 10 and 20 Hz. This type of stimulation did not improve the tinnitus.

Next, transcutaneous electrical nerve stimulation (TENS) was used. TENS had a beneficial effect on her tinnitus, decreasing the tinnitus intensity to 7/10 on the left side and removing the aggressivity of the sound, as well as stabilizing the tinnitus. TENS at 6 and 40 Hz, 50 μs pulse width have the best effect. The patient described that the tinnitus sounds less chaotic, less fluctuating. Stress or fatigue however kept worsening the tinnitus, but the spontaneous variability in the tinnitus has disappeared. After three months of TENS, the patients first noticed she can recognize the sound of a car and a dog barking, but only when the TENS is on. One month later she can recognize her husbands voice, and after one year of TENS she can recognize some words, but also only when the TENS is on.

Next, a bilateral subcutaneous occipital electrode was implanted (quatrode, ANS Medical) and connected to an internal pulse generator (Genesis, ANS Medical). This improved the tinnitus even more at stimulation settings 6 Hz, 5 μs pulse width and intensities between 2 and 6 mAmp, however without auditory agnosia improvement. Stimulation at 18 Hz has better effects, with even better tinnitus suppression and immediate auditory agnosia and word deafness improvement.

Thus, electrical stimulation of the somatosensory system can be used to treat tinnitus, as well as improve auditory perception, such as auditory agnosia and word deafness by activation of the extralemniscal auditory connections to the somatosensory system.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Foxe et al., Cognitive Brain Research 10:77-83 (2000)
Fu et al., The Journal of Neuroscience 23(20):7510-7515 (2003)
Jones, Trends in Neuroscience, Vol. 24, No. 10:595-601 (2001)
Moller et al., (1992), Laryngoscope. 102(10):1165-71
Moller and Rollins, Neuroscience Letters 319:41-44 (2002)
Moller et al., Laryngoscope 102:1165-1171 (1992)
Mirz et al., Hearing Research 134:133-144 (1999)
Norton, BioMedical Engineering OnLine 2:6 (2003)
Tardif et al., Neuroscience 116:1111-1121 (2003)
Wallhausser-Franke et al., Experimental Brain Research 153: 649-654 (2003)
Zhang et al., Experimental Brain Research 153:655-660 (2003)
U.S. Pat. No. 5,496,369
U.S. Pat. No. 5,697,975
U.S. Pat. No. 5,713,847
U.S. Pat. No. 5,735,885
U.S. Pat. No. 5,788,656
U.S. Pat. No. 6,210,321
U.S. Pat. No. 6,456,886
U.S. Pat. No. 6,656,172
International Pub. No. WO 01/08617

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of alleviating auditory dysfunction comprising:
positioning at least one stimulation lead having a plurality of electrodes within a patient such that at least one electrode of the stimulation lead is positioned in subcutaneous tissue of an occipital area of the patient and the stimulation lead is positioned below the skin and superior to the periosteum; and
generating electrical pulses from an implantable pulse generator through the stimulation lead to electrically stimulate the occipital area to treat the auditory dysfunction in the patient, wherein the generating electrical pulses comprises generating a burst stimulation pattern of pulses, wherein each burst in the burst stimulation pattern comprises a plurality of pulses at a high pulse frequency, adjacent bursts in the stimulation pattern are separated by a quiescent interval, and the quiescent interval is repeated at a frequency of 40 Hz or less.

2. The method of claim 1, wherein the lead is positioned within the C2 dermatome.

3. The method of claim 1, wherein the lead is positioned at the back of the patient's head at about the level of the ear.

4. The method of claim 1, wherein the lead is positioned within the subcutaneous tissue of the C2 dermatome above the periosteum.

5. The method of claim 1 wherein the auditory dysfunction is tinnitus, hyperacousis, phonophobia, misophonia, auditory agnosia, auditory spatial dysfunction or auditory hallucinations.

6. The method of claim 1 wherein the auditory dysfunction is tinnitus.

7. The method of claim 1 wherein the auditory dysfunction is auditory agnosia.

8. The method of claim 1, wherein the stimulation lead is a percutaneous lead.

9. The method of claim 1, wherein the stimulation lead is a paddle lead.

10. The method of claim 1, wherein the stimulation lead and the pulse generator are integrated in a single device.

* * * * *